(12) United States Patent
Govari et al.

(10) Patent No.: US 11,844,617 B2
(45) Date of Patent: *Dec. 19, 2023

(54) OPTIMIZING MAPPING OF ECG SIGNALS RETROSPECTIVELY BY DETECTING INCONSISTENCY

(71) Applicant: Biosense Webster (Israel) Ltd., Yokneam (IL)

(72) Inventors: Assaf Govari, Haifa (IL); Vadim Gliner, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/842,105

(22) Filed: Jun. 16, 2022

(65) Prior Publication Data

US 2022/0318576 A1 Oct. 6, 2022

Related U.S. Application Data

(63) Continuation of application No. 16/674,921, filed on Nov. 5, 2019, now Pat. No. 11,366,991.

(51) Int. Cl.
*A61B 5/28* (2021.01)
*A61B 5/287* (2021.01)
(Continued)

(52) U.S. Cl.
CPC .............. *A61B 5/287* (2021.01); *A61B 5/316* (2021.01); *A61B 5/327* (2021.01); *A61B 5/339* (2021.01);
(Continued)

(58) Field of Classification Search
None
See application file for complete search history.

(56) References Cited

U.S. PATENT DOCUMENTS 3,456,182 A1 6/2013 Bar-Tal et al.
11,366,991 B2 * 6/2022 Govari ................. A61B 5/7203
(Continued)

FOREIGN PATENT DOCUMENTS

EP 2901953 A1 8/2015
EP 3384835 A1 10/2018

OTHER PUBLICATIONS

EP Search Report dated Mar. 15, 2021, Issued in EP Application No. 20 20 5762 (BIO6197EPEPA1); 12 pages.
(Continued)

*Primary Examiner* — Ankit D Tejani
(74) *Attorney, Agent, or Firm* — Troutman Pepper Hamilton Sanders LLP

(57) ABSTRACT

A system includes signal acquisition circuitry and a processor. The signal acquisition circuitry is configured to receive multiple intra-cardiac signals acquired by multiple electrodes of an intra-cardiac probe in a heart of a patient. The processor is configured to perform a sequence of annotation-visualization operations at subsequent times, by performing, in each operation: extracting multiple annotation values from the intra-cardiac signals, selecting a group of the intra-cardiac signals, identifying in the group one or more annotation values that are statistically deviant by more than a predefined measure of deviation, and visualizing the annotation values to a user, while omitting and refraining from visualizing the statistically deviant annotation values. The processor is further configured to assess, over one or more of the annotation-visualization operations, a rate of omissions of annotation values, and to take a corrective action in response to detecting that the rate of omissions exceeds a predefined threshold.

20 Claims, 8 Drawing Sheets

(51) Int. Cl.
  *A61B 5/339*  (2021.01)
  *A61B 5/316*  (2021.01)
  *A61B 5/00*   (2006.01)
  *A61B 5/327*  (2021.01)
  *G06F 18/2433* (2023.01)

(52) U.S. Cl.
  CPC .......... *A61B 5/7203* (2013.01); *A61B 5/7221* (2013.01); *A61B 5/743* (2013.01); *G06F 18/2433* (2023.01)

(56) References Cited

U.S. PATENT DOCUMENTS

| | | |
|---|---|---|
| 2004/0039293 A1 | 2/2004 | Porath et al. |
| 2005/0143634 A1 | 6/2005 | Baker, Jr. et al. |
| 2009/0089048 A1 | 4/2009 | Pouzin |
| 2015/0208942 A1 | 6/2015 | Bar-Tal et al. |
| 2015/0366476 A1 | 12/2015 | Laughner et al. |
| 2016/0089048 A1 | 3/2016 | Brodnick et al. |
| 2016/0128785 A1 | 5/2016 | Nanthakumar et al. |
| 2017/0042436 A1 | 2/2017 | Harlev et al. |
| 2017/0311833 A1 | 11/2017 | Afonso et al. |
| 2019/0030332 A1 | 1/2019 | Ghosh et al. |

OTHER PUBLICATIONS

Roney Caroline H. et al: "An automated algorithm for determining conduction velocity, wavefront direction and origin of focal cardiac arrhythmias using a multipolar catheter", 2014 36th Annual International Conference of the IEEE Engineering in Medicine and Biology Society, IEEE, Aug. 26, 2014, pp. 1583-1586, XP032674695, DOI: 10.1109/EMBC.2014.6943906 *abstract *.

* cited by examiner

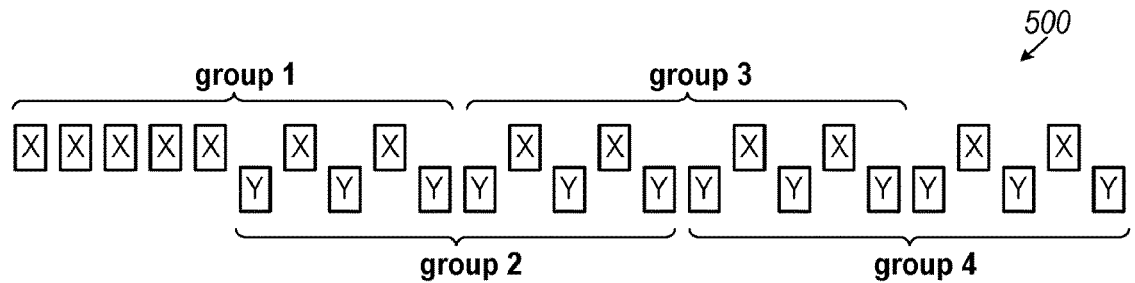
FIG. 5A - input LAT values
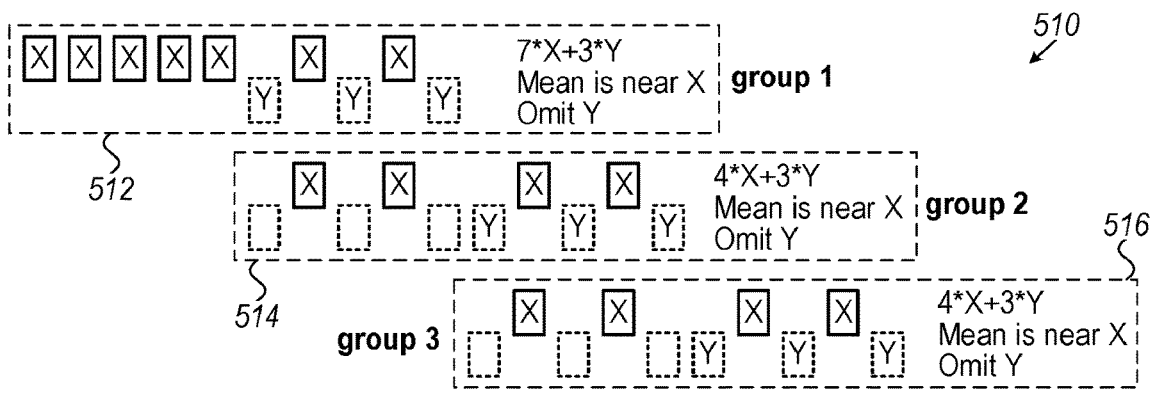
FIG. 5B - groups mean - error propagation
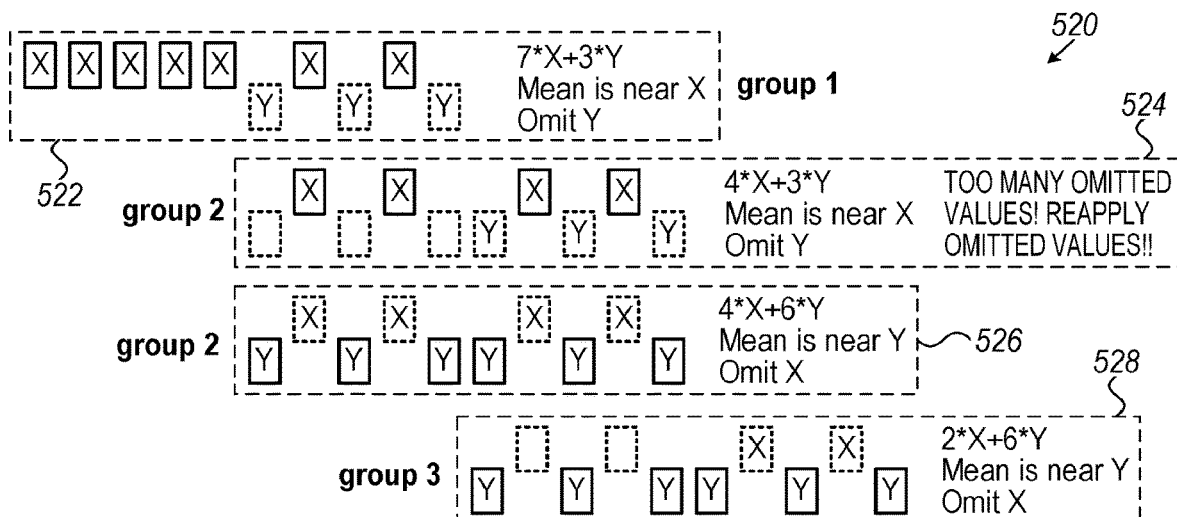
FIG. 5C - groups mean – with omitted values reapplication

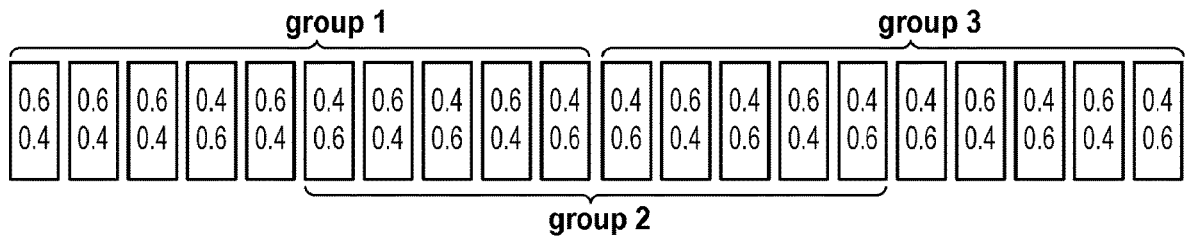
FIG. 6A - input LAT value probabilities
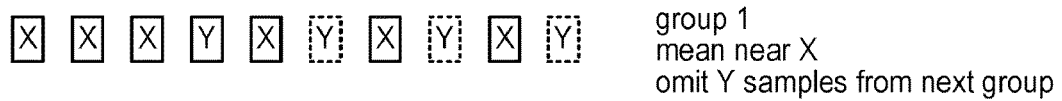
FIG. 6B - group 1 initial LAT values
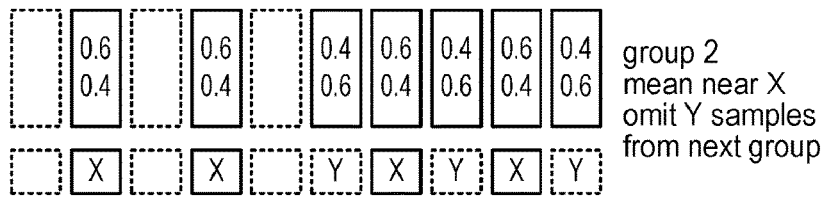
FIG. 6C - group 2 initial LAT values
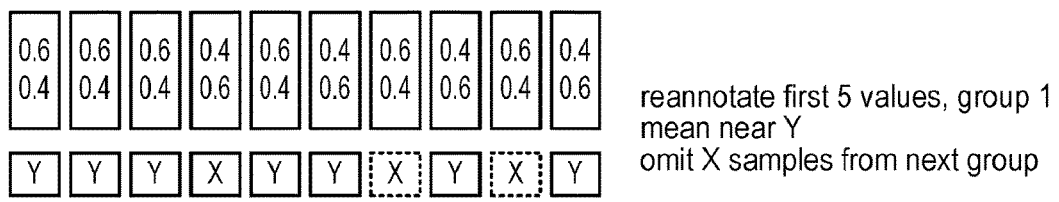
FIG. 6D - group 2 re-annotation
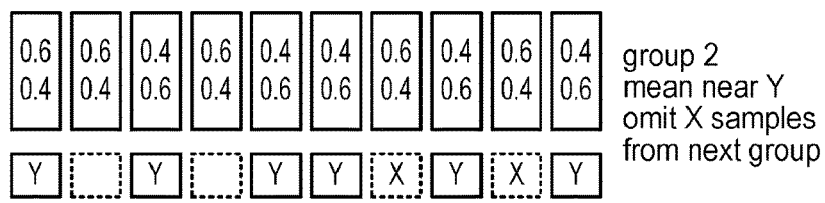
FIG. 6E - group 2 reassessed

OPTIMIZING MAPPING OF ECG SIGNALS RETROSPECTIVELY BY DETECTING INCONSISTENCY

CROSS-REFERENCE TO RELATED APPLICATIONS

The present application is a continuation application of U.S. patent application Ser. No. 16/674,921 filed Nov. 5, 2019. The entire contents of which are hereby incorporated by reference.

This application is related to a U.S. patent application entitled "Using Statistical Characteristics of Multiple Grouped ECG Signals to Detect Inconsistent Signals," U.S. patent application Ser. No. 16/674,911, filed on Nov. 5, 2019, whose disclosure is incorporated herein by reference.

FIELD OF THE INVENTION

The present invention relates generally to intrabody medical procedures and instruments, and particularly to intrabody cardiac electrocardiogram (ECG) sensing.

BACKGROUND OF THE INVENTION

When measuring and annotating internal-electrocardiogram (iECG) signals that are generated by a large number of electrodes, it may be desirable to process the signals (e.g., by a computer), in order to reduce the embedded noise.

Various methods exist for such iECG signal processing. For example, US Patent Application 2016/0089048 describes an automatic method of determining local activation time (LAT) of four or more multi-channel cardiac electrogram signals which include a Ventricular channel, a mapping channel and a plurality of reference channels.

SUMMARY OF THE INVENTION

An embodiment of the present invention that is described herein provides a system including signal acquisition circuitry and a processor. The signal acquisition circuitry is configured to receive multiple intra-cardiac signals acquired by multiple electrodes of an intra-cardiac probe in a heart of a patient. The processor is configured to perform a sequence of annotation-visualization operations at subsequent times, by performing, in each operation: extracting multiple annotation values from the intra-cardiac signals, selecting a group of the intra-cardiac signals, identifying in the group one or more annotation values that are statistically deviant by more than a predefined measure of deviation, and visualizing the annotation values to a user, while omitting and refraining from visualizing the statistically deviant annotation values. The processor is further configured to assess, over one or more of the annotation-visualization operations, a rate of omissions of annotation values, and to take a corrective action in response to detecting that the rate of omissions exceeds a predefined threshold.

In some embodiments, the processor is configured to take the corrective action by re-applying one or more of the omitted annotation values and re-identifying the statistically deviant annotation values. In some embodiments, the processor is configured to take the corrective action by re-extracting one or more of the annotation values from the intra-cardiac signals.

In an embodiment, the processor is configured to define the measure of the deviation in terms of a standard score of the annotation values. In another embodiment, the processor is configured to define the measure of the deviation in terms of one or more percentiles of the annotation values.

In an example embodiment, in a given annotation-visualization operation, the processor is configured to calculate deviations of the annotation values over intra-cardiac signals acquired by a selected subset of spatially-related electrodes located no more than a predefined distance from one another in the heart. In another embodiment, in calculating deviations of the annotation values for a given annotation-visualization operation, the processor is configured to average the intra-cardiac signals over multiple temporally-related cardiac cycles that occur within a predefined time duration.

In yet another embodiment, in a given annotation-visualization operation, the processor is configured to correct one or more of the annotation values in a given intra-cardiac signal, acquired by a given electrode in the group, to compensate for a displacement of the given electrode relative to the other electrodes in the group.

In some embodiments, the annotation values include Local Activation Times (LATs). In some embodiments, the processor is configured to visualize the annotation values by overlaying the annotation values, excluding the statistically deviant annotation values, on a model of the heart.

There is additionally provided, in accordance with an embodiment of the present invention, a method including receiving multiple intra-cardiac signals acquired by multiple electrodes of an intra-cardiac probe in a heart of a patient. A sequence of annotation-visualization operations is performed at subsequent times, by performing, in each operation: (i) extracting multiple annotation values from the intra-cardiac signals, (ii) selecting a group of the intra-cardiac signals, (iii) identifying in the group one or more annotation values that are statistically deviant by more than a predefined measure of deviation, and (iv) visualizing the annotation values to a user, while omitting and refraining from visualizing the statistically deviant annotation values. A rate of omissions of annotation values is assessed over one or more of the annotation-visualization operations. A corrective action is taken in response to detecting that the rate of omissions exceeds a predefined threshold.

The present invention will be more fully understood from the following detailed description of the embodiments thereof, taken together with the drawings in which:

BRIEF DESCRIPTION OF THE DRAWINGS

FIG. 5A is a diagram that schematically illustrates the annotation of a series of LAT values from a group of spatially related electrodes in an electro-anatomical system, according to embodiments of the present invention;

FIG. 5B is a diagram that schematically illustrates statistical characteristics calculation of the LAT values that the processor receives (in FIG. 5A) when no corrective action is taken, according to embodiments of the present invention;

FIG. 5C is a diagram that schematically illustrates avoidance of error propagation by reapplying omitted values, according to embodiments of the present invention;

FIG. 6A is a diagram that schematically illustrates probabilities of LAT values of a series of signals that are acquired by a group of spatially related electrodes in an electro-anatomical system, according to embodiments of the present invention;

FIG. 6B is a diagram that schematically illustrates annotation of LAT values for Group-1 signals, according to an embodiment of the present invention;

FIG. 6C is a diagram that schematically illustrates annotation of LAT values for Group-2 signals, according to an embodiment of the present invention;

FIG. 6D is a diagram that schematically illustrates re-annotation of the signals of Group-1, according to embodiments of the present invention;

FIG. 6E is a diagram that schematically illustrates re-calculation of Group-2 annotation values following reannotation, according to an embodiment of the present invention.

DETAILED DESCRIPTION OF EMBODIMENTS

Overview

Figure 1:
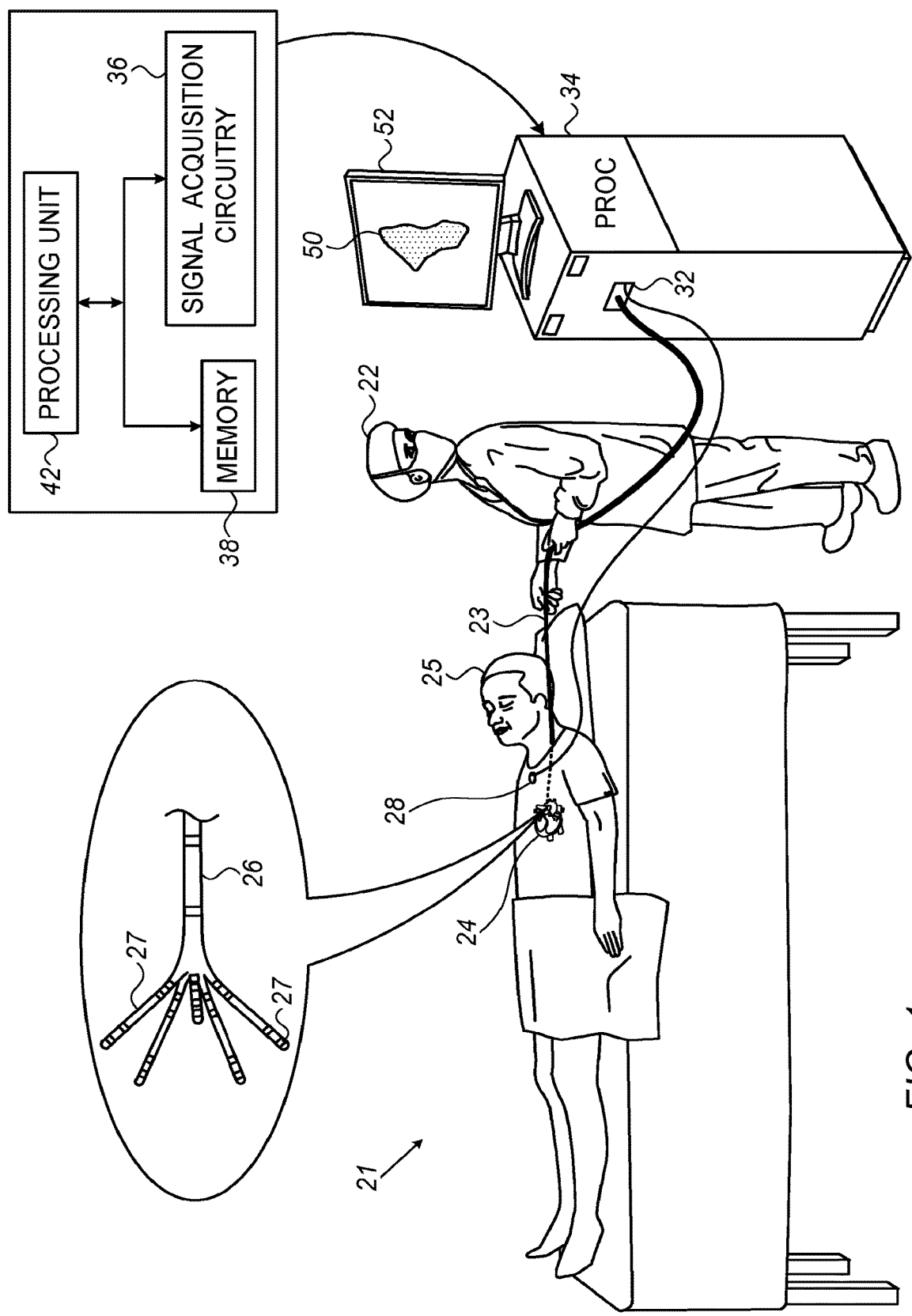
FIG. 1 is a schematic, pictorial illustration of an electro-anatomical system for multi-channel measurement of intra-cardiac ECG signals, in accordance with an embodiment of the present invention.

Intra-cardiac probe-based (e.g., catheter-based) cardiac diagnostic and therapeutic systems may measure multiple intra-cardiac signals, such as electrocardiograms (ECG), during an invasive procedure. Such systems may acquire the multiple intra-cardiac signals using electrodes (also referred to hereinafter as "distal electrodes") that are fitted at the distal end of the probe. The measured signals may be used to provide a physician with visual cardiac information such as 3-D mapping of the source of pathological electrical patterns within the heart of the patient, and to support corrective medical procedures such as ablation.

The measured signals are typically weak, with a low Signal to Noise Ratio (SNR). Moreover, the galvanic connection of some of the electrodes with the tissue may be poor or non-existent. On the other hand, many electrodes are used, and, hence, there may be some redundancy in the data that the system receives from the electrodes.

Embodiments of the present invention that are disclosed herein provide intra-cardiac probe-based electro-anatomical measurement and analysis systems and methods that use statistical characteristics of the signals that the distal electrodes collect, to improve the quality and reliability of the collected data.

In the description hereinbelow we will refer to annotation value of Local Activation Time (LAT). The disclosed techniques, however, are not limited to LAT; in various embodiments of the present invention, annotation values of various other suitable signal parameters may be used.

In some embodiments according to the present invention, a processor extracts annotation values (e.g., the LAT) of the signals, and then calculates statistical characteristics of the LAT values of a group of signals that are acquired by a corresponding group of electrodes (which may comprise all or some of the electrodes). In an embodiment, the statistical characteristics comprise the mean of the LAT values of the group of signals (e.g., $\dot{x}=\Sigma x/n$); in other embodiments the characteristics further comprise the standard deviation (e.g., $\sigma=\sqrt{(\Sigma(x-\dot{x})^2/n)}$) of the group. The processor then uses statistical methods to determine, for each one of the group of signals, whether annotation values of signals are valid values, or values that should be ignored.

In another embodiment, the statistical characteristics comprise the quartiles of the group of LAT values. The processor calculates the first and the third quartiles Q1, Q3, and then ignores all values that are lower than Q1 or higher than Q3 (a first quartile (Q1) is defined as the middle number between the smallest number and the median of a data set; a third quartile (Q3) is the middle value between the median and the highest value of the data set). Alternatively, the processor may define the measure of deviation of the LAT values in terms of any other suitable percentile (or multiple percentiles) of the LAT values. Further alternatively, any other suitable process that discards outlier LAT values can be used.

The technique disclosed hereinabove assumes that, devoid of noise and irregular galvanic connections, the electrodes of the group exhibit similar annotation values. Typically, the annotation values acquired by electrodes that are remote from each other may vary substantially. In addition, signals from each electrode may be annotated periodically, with each heartbeat ("cardiac cycle"), and annotation values derived from cardiac cycles that are temporally remote from each other may vary. In an embodiment, the group of signals is inter-related. In some embodiments, a tracking system measures the geometrical location of the electrodes, and the group comprises annotation values derived from neighboring electrodes only ("spatially related," i.e., electrodes that are located no more than a predefined distance from one another). In other embodiments the group comprises annotation values derived from neighboring cardiac cycles only ("temporally related," i.e., cardiac cycles that all occur within no more than a predefined time duration); and, in an embodiment, the group comprises values that are both spatially and temporally related (will be referred to, in short, as "related values").

In some embodiments, the processor, after calculating the statistical characteristics of the group of related LAT values, omits LAT values that are statistically deviant in the group, e.g., substantially different from the mean value of the group of values (the group of the remaining LAT values will be referred to as the group of valid LAT values). Thus, LAT values that correspond to poorly connected electrodes, or to electrodes that are subject to extreme noise, may be eliminated from the group of valid LAT values.

In embodiments, to determine whether a LAT value is statistically deviant from the mean LAT of a group of signals, the processor measures the deviation of annotated LAT valued from the mean of the group of LAT values. In an embodiment, the measure of the deviation is the Standard Score of the value (defined as the difference between the value and the mean, divided by the standard deviation), which is compared to preset limits. For-example, values that are larger than the mean by more than 3.5 standard deviations (standard score=3.5), or lower than the mean by more than 1.5 standard deviations (standard score=−1.5) may be considered statistically deviant and thus omitted. In another embodiment, the processor omits values that are lower than the first quartile or higher than the third quartile.

In some embodiments of the present invention, the processor may mitigate the variance in LAT values of spatially related electrodes due to the different time delays of cardiac signal propagation within the heart. According to embodiments, the processor may correct the LAT annotation acquired by a given electrode, by compensating for the displacement of the given electrode relative to the other electrodes, so as to cancel the difference in propagation delay.

An electrocardiogram signal may sometimes be ambiguously interpreted, and two LAT values may be annotated (a correct value and a wrong value), with different probabilities. For example, the signal may have two peaks that are close to each other. Consequently, in some cases the calculated mean of a subset may be closer to the wrong LAT value than to the correct LAT value.

In some embodiments, the processor repeats the selection of groups over time (for example, once every 32 cardiac cycles), with partial overlap between subsequent groups. The processor forms new groups by removing some (but not all) of the old values (e.g., values extracted in the oldest 16 cardiac cycles) and adding new values (e.g., values extracted in the newest 16 cardiac cycles) ("old" and "new", in this context, refer to the sequential number of the cardiac cycle in which a signal was acquired). If the mean of the first group that the processor calculates is wrong (for example due to the ambiguity of the signal), the processor may omit overlapping LAT values that are correct from the next group, disrupting the mean calculation, and, hence, the error in the first mean calculation may propagate to later groups, although the newly annotated LAT values may be correct.

Embodiments according to the present invention that are disclosed herein avoid such error propagation. In an embodiment, the processor monitors the number of omitted LAT values, and, responsive to the rate at which values are omitted, the processor may decide to consider the omitted values in the calculation of the new average, so that the error will not propagate beyond the erroneous group. In other embodiments, if the processor detects a large number of omitted values, the processor may reannotate some of the values with an alternative interpretation of the corresponding signals, and then recount the omitted values; the processor will choose the alternative annotation if the number of omitted values will decrease.

In summary, a processor according to embodiments of the present invention may improve the quality and reliability of a group of annotation values of spatially and/or temporally related inter-cardiac signals, by calculating statistical characteristics of the annotation values, comparing the annotation values to the group mean, and omitting from the group of valid values, values that are remote from the mean. In some embodiments, prior to statistical characteristics calculation, the processor may modify the group of annotation values to correct for propagation delays of the signals. To avoid error propagation, the processor may monitor the number of omitted values, and, responsive to the rate at which omissions occur, may reevaluate the group, with the previously omitted values reinstated; in other embodiments, responsive to the rate of omitted values, the processor may reannotate the values, looking for an alternative LAT interpretation.

System Description

FIG. 1 is a schematic, pictorial illustration of an electro-anatomical system 21 for multi-channel measurement of intra-cardiac ECG signals, in accordance with an embodiment of the present invention. In some embodiments, system 21 is used for electro-anatomical mapping of a heart.

FIG. 1 depicts a physician 22 using an electro-anatomical catheter 23 to perform an electro-anatomical mapping of a heart 24 of a patient 25. Catheter 23 comprises, at its distal end, one or more arms 26, which may be mechanically flexible, to each of which are coupled one or more distal electrodes 27. As would be appreciated, although FIG. 1 depicts a catheter with five arms, other types of catheters may be used in alternative embodiments according to the present invention. The electrodes are coupled, through an interface 32, to a processor 34.

During the electro-anatomical mapping procedure, a tracking system is used to track the intra-cardiac locations of distal electrodes 27, so that each of the acquired electrophysiological signals may be associated with a known intra-cardiac location. An example of tracking system is Active Current Location (ACL), which is described in U.S. Pat. No. 8,456,182. In the ACL system, a processor estimates the respective locations of the distal electrodes based on impedances measured between each of distal electrodes 27 and a plurality of surface electrodes 28 that are coupled to the skin of patient 25 (For ease of illustration, only one surface-electrode is shown in FIG. 1.). The processor may then associate any electrophysiological signal received from distal electrodes 27 with the location at which the signal was acquired.

In some embodiments, multiple distal electrodes 27 acquire intra-cardiac ECG signals from tissue of a cardiac chamber of heart 24. The processor comprises a signal acquisition circuitry 36 that is coupled to receive the intra-cardiac signals from interface 32, a memory 38 to store data and/or instructions, and a processing unit 42 (e.g., a CPU or other processor).

Signal acquisition circuitry 36 digitizes the intra-cardiac signals so as to produce multiple digital signals. The Acquisition Circuitry then conveys the digitized signals to processing unit 42, included in processor 34.

Among other tasks, processing unit 42 is configured to extract annotation parameters from the signals, calculate statistical characteristics such as mean value of the annotated parameters for groups of neighboring signals that are likely to be similar (in the current context, neighboring signals refers to signals from electrodes located close to each other ("spatially related"), and/or to annotation values extracted from cardiac cycles that are close to each other in time ("temporally related")).

The processing unit is further configured, after calculating the statistical characteristics, to drop (i.e., omit) annotation values that are likely to be invalid from the group (such as annotation from electrodes with poor galvanic connection, or subject to an intense temporal noise). The remaining annotation values will be referred to hereinbelow as "valid annotation values."

Processor 34 visualizes the valid annotation values, i.e., the annotation values excluding the statistically deviant annotation values that have been omitted, to a user. In some embodiments, processor 34 visualizes the valid annotation values, for example, by overlaying them on an electro-anatomical map 50 of the heart and displaying the map to physician 22 on a screen 52. Alternatively, processor 34 may visualize the valid annotation values (after omitting the invalid annotation values) in any other suitable way.

The example illustration shown in FIG. 1 is chosen purely for the sake of conceptual clarity. In alternative embodiments of the present invention, for example, position measurements can also be done by applying a voltage gradient between pairs of surface electrodes 28 and measuring, with distal electrodes 27, the resulting potentials (i.e., using the CARTO®4 technology produced by Biosense-Webster, Irvine, California). Thus, embodiments of the present invention apply to any position sensing method.

Other types of catheters, such as the Lasso® Catheter (produced by Biosense-Webster), or a basket catheter, may equivalently be employed. Contact sensors may be fitted at the distal end of electro-anatomical catheter 23. Other types of electrodes, such as those used for ablation, may be utilized in a similar way on distal electrodes 27 to acquire intra-cardiac electrophysiological signals.

FIG. 1 mainly shows parts relevant to embodiments of the present invention. Other system elements, such as external ECG recording electrodes and their connections are omitted. Various ECG recording system elements are omitted, as well as elements for filtering, digitizing, protecting circuitry, and others.

In an optional embodiment, a read-out application-specific integrated circuit (ASIC) is used for measuring the intra-cardiac ECG signals. The various elements for routing signal acquisition circuitry 36 may be implemented in hardware, e.g., using one or more discrete components, such as field-programmable gate arrays (FPGAs) or ASICs. In some embodiments, some elements of signal acquisition circuitry 36 and/or processing unit 42 may be implemented in software, or by using a combination of software and hardware elements.

Processing unit 42 typically comprises a general-purpose processor with software programmed to carry out the functions described herein. The software may be downloaded in electronic form, over a network, for example, or it may, alternatively or additionally, be provided and/or stored on non-transitory tangible media, such as magnetic, optical, or electronic memory.

Related Annotation Values

Related Annotation Values are derived from spatially related electrodes (e.g., electrodes that are geometrically close to each other, i.e., located no more than a predefined distance from one another) and/or from temporally related signals (e.g., values extracted from cardiac cycles that are close to each other, i.e., occur within no more than a predefined time duration). More precisely, related annotation values are annotation values for which the combined distance, comprising the geometrical distance between the electrodes and the temporal distance between the cardiac cycles, is below some predefined threshold.

Figure 2:
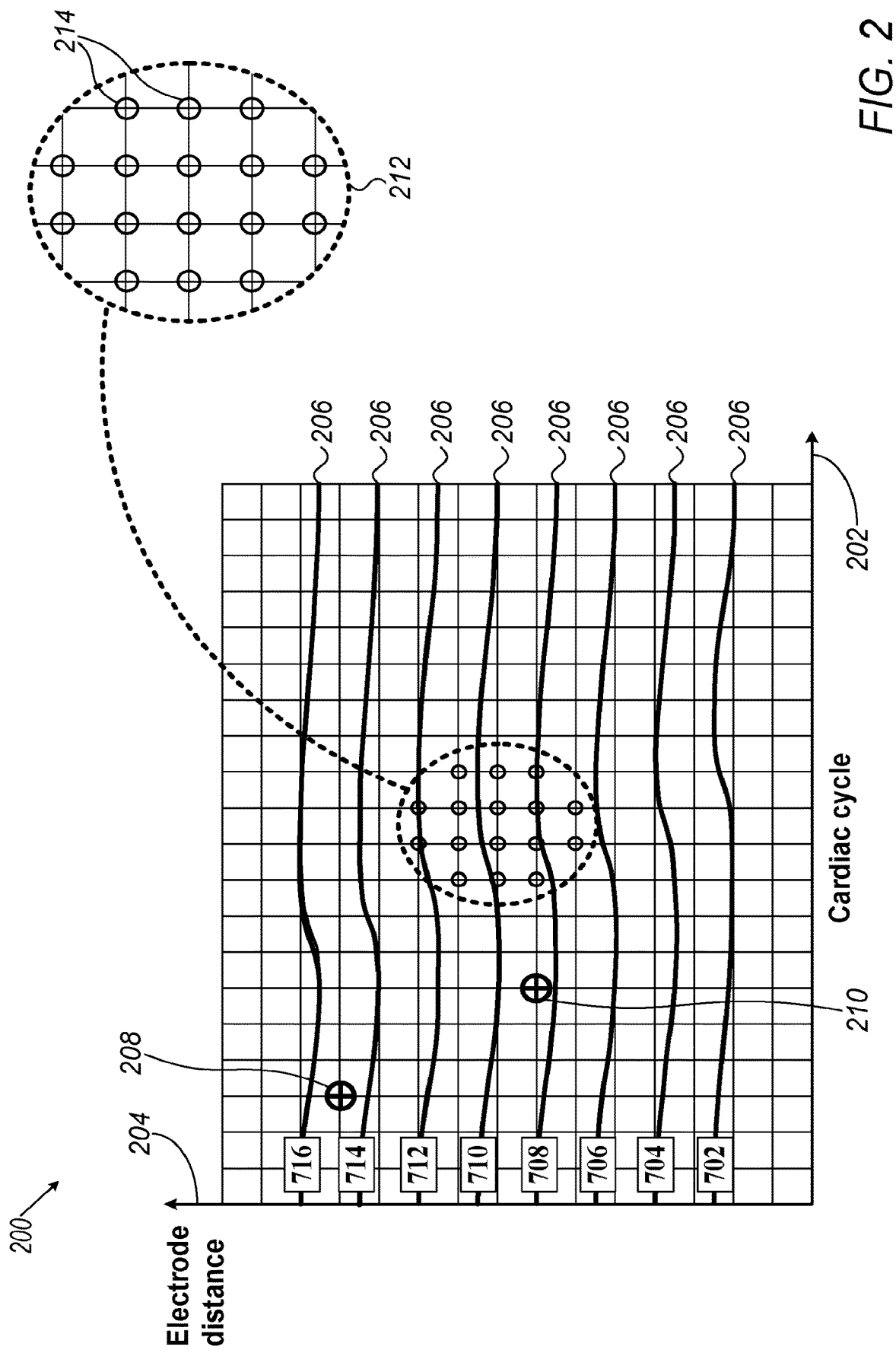
FIG. 2 is a diagram that schematically illustrates acquisition of signals by multiple electrodes at multiple cardiac cycles, in accordance with an embodiment of the present invention.

FIG. 2 is a diagram 200 that schematically illustrates acquisition of signals by multiple electrodes at multiple cardiac cycles. A horizontal axis 202 shows the cardiac cycle (each vertical line is one cardiac cycle), and a vertical axis 204 shows the distance of the electrode from a reference point (only one spatial dimension is shown; as would be appreciated, two or three dimensions may be used in practice, but are not shown, for clarity). According to the example embodiment illustrated in FIG. 2, there are electrodes in all horizontal lines, and LAT annotation values are registered for all intersections of horizontal and vertical lines (each intersection will be referred hereinbelow to as a LAT-point).

Curves 206 are equi-LAT lines, showing the location of the indicated LAT values, and the electrodes are likely to measure, at the corresponding cardiac cycles, values interpolated from the neighboring equi-LAT curves. For example, the expected registered value of LAT-point 208 (which is vertically half-way between equi-LAT lines 714 and 716) is 715, whereas the expected registered value of LAT-point 210 is 708.5.

As can be seen, the LAT values of neighboring vertical lines and of neighboring horizontal lines are similar. Circle 212 represents a group of related LAT values 214, that are close to each other in terms of geometrical (vertical) and temporal (horizontal) distances.

The example illustration shown in FIG. 2 is simplified and shown purely for the sake of conceptual clarity. In alternative embodiments, for example, the distance between the electrodes is not uniform, and, the group of related signals may not be a circle.

Figure 3A:
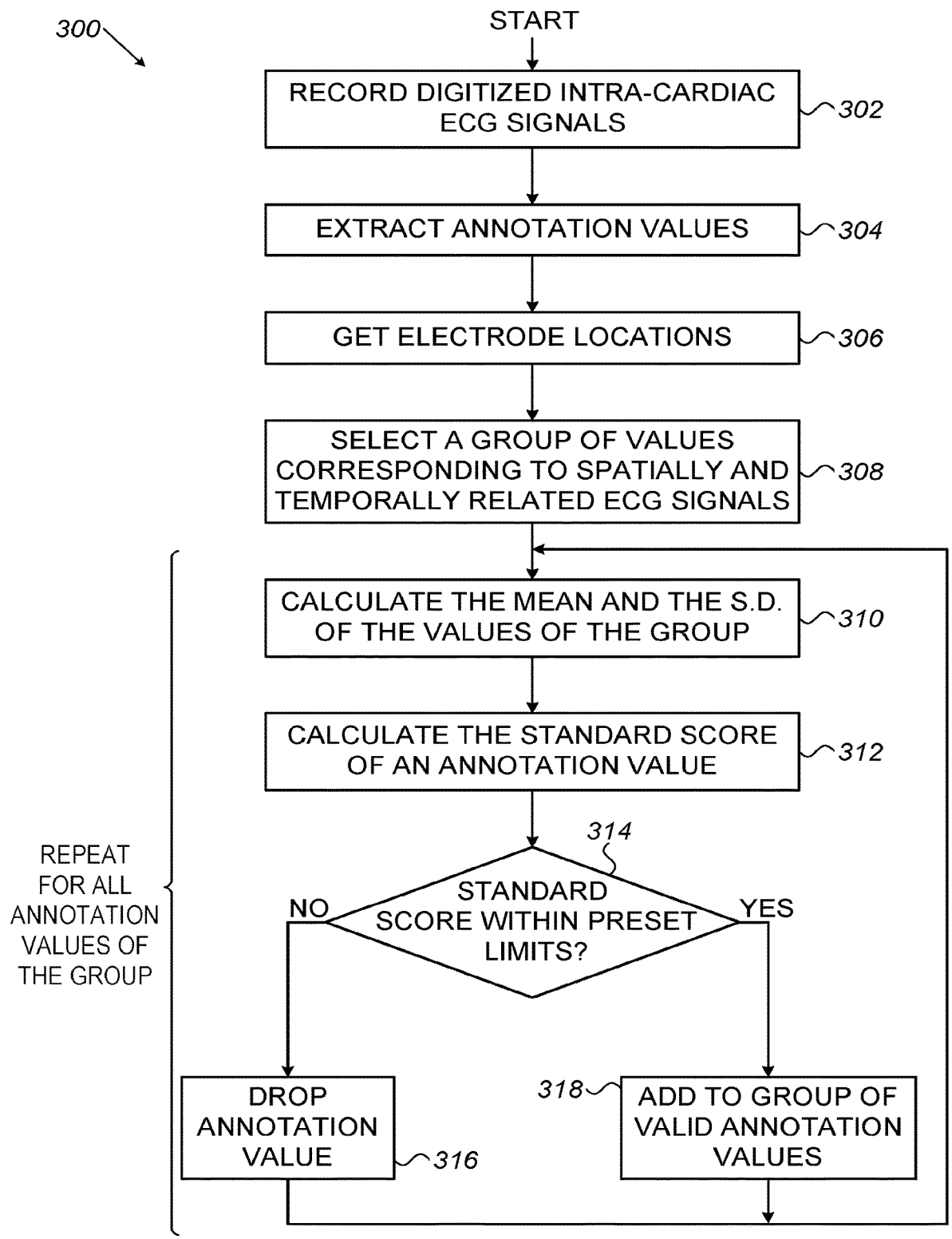
FIG. 3A is a flow chart that schematically illustrates a first method for enhancing the reliability of annotation values, in accordance with an embodiment of the present invention.

FIG. 3A is a flow chart 300 that schematically illustrates a first method for enhancing the reliability of annotation values, according to embodiments of the present invention. The flow is executed by processor 34 (FIG. 1). The flow starts at a Recording Signals step 302, wherein the processor records ECG signals monitored by electrodes 27 and acquired by acquisition circuitry 36 (FIG. 1). Next, at an Extracting Annotation Values step 304, the processor calculates the annotation values for each electrode and each cardiac cycle.

The processor then enters a Getting Electrode Location step 306, wherein the location of the electrodes is acquired (e.g., using the ACL technique), and the spatial location of each electrode is registered, and then enters a Selecting Group step 308.

In step 308, the processor selects a group of related annotation values. As described hereinabove, the group comprises annotation values that are likely to be similar, from spatially and/or temporally related signals.

Next, in a Calculating Mean and SD step 310, the processor calculates the average and standard deviation for all annotation values of the group. In the present context, any suitable type of mean can be used, such as an arithmetic mean, a geometric mean, a median, a Root Mean Square (RMS) value, a center of mass, or any other.

The processor then, repeatedly for each annotation value of the group, sequentially enters steps 312, 314, and either step 316 or step 318. In a Calculating Standard Score step 312, the processor calculates the standard score of the annotation value (e.g., by dividing the difference between the annotation value and the mean by the standard deviation). In a Comparing Standard Score step 314 the processor compares the standard score calculated in step 312 to preset limits. In a Dropping Value step 316, which is entered if the standard score exceeds a preset limit, the processor drops the statistically deviant annotation value; and, in an Adding Value step 318, which is entered if the standard score is within the preset limits, the processor adds the annotation value to a group of valid annotation values.

The processor repeats the sequence of steps 312, 314 and either step 316 or step 318 for all annotation values of the group. The flow chart may then repeat (from step 308) for other groups of related electrodes.

When the flow ends, groups of valid annotation values replace the original groups, with better reliability, as extreme values (for example, from electrodes with poor galvanic connection) are omitted.

Figure 3B:
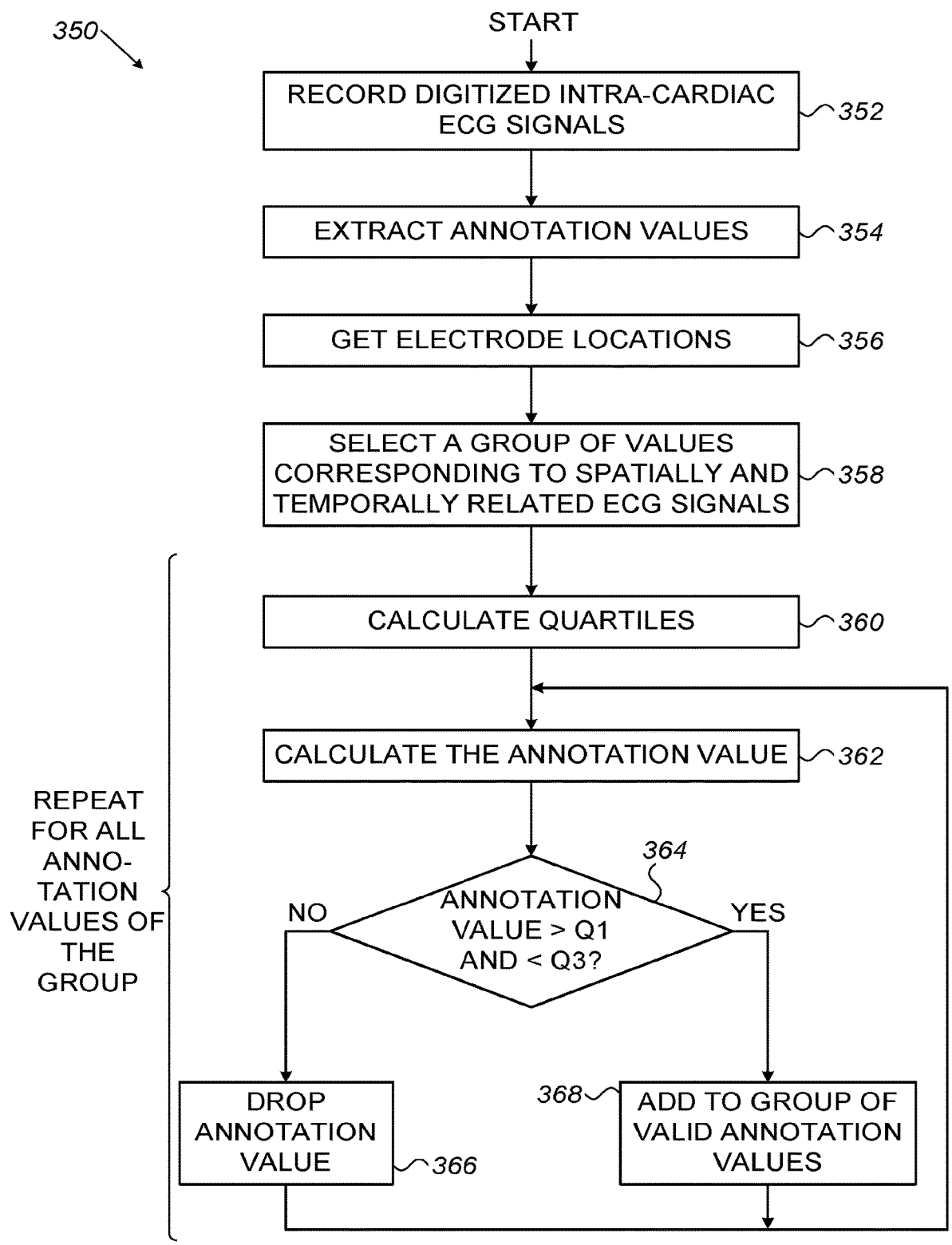
FIG. 3B is a flow chart that schematically illustrates a second method for enhancing the reliability of annotation values, in accordance with an embodiment of the present invention.

FIG. 3B is a flow chart 350 that schematically illustrates a second method for enhancing the reliability of annotation values, according to embodiments of the present invention. The method illustrated in FIG. 3B differs from the method illustrated in FIG. 3A only in the statistical characteristics and the selection of omitted values. Hence, steps 302 to 318 illustrated in FIG. 3A are identical, respectively, to steps 352 to 368 of FIG. 3B, except for steps 360 and 364, which are different from steps 310, 314 of FIG. 3A, and will be described hereinbelow.

In a Calculating Quartiles step 362, processing unit (FIG. 1) calculates the first and the third quartiles (Q1 and Q3) of the group of LAT values (Q1 is defined as the middle number between the smallest number and the median of the group of LAT values; Q3 is the middle value between the median and the highest value of group of LAT values).

In a Comparing Annotation Value step 364, the processing units compares the annotated LAT value to Q1 and to Q3. If the value is smaller than Q1 or higher than Q3, the processing unit will enter Dropping Annotation Value step 366, wherein if the value is between Q1 and Q3, will enter Adding Value step 368.

The example flow charts shown in FIGS. 3A, 3B are chosen purely for the sake of conceptual clarity. In alternative embodiments, for example, annotation values may be extracted when the signal is acquired (rather than after the signal is recorded). In an embodiment, the selection of the signals of the group may be done by the physician; in other embodiments the processor will select the group, according to an area and/or a time range that the physician indicates.

In some embodiments, step 318 (368 in FIG. 3B) is not needed—the processor will, in step 316 (366), drop extreme values from the group, and when the flow is completed only the good values will remain. In other embodiments, all annotation values are initially marked as invalid, and step 316 (366) is not needed.

In some embodiments, other statistical characteristics that are used, different than those described above; for example, in an embodiment, octiles rather than quartiles may be used, and the processing unit may omit values lower than the first octile or higher than the last octile. Further alternatively, any other suitable percentile can be used.

Any other suitable statistical methods to detect and omit extreme values may be used in alternative embodiments.

Propagation Delay Compensation

In some embodiments, the technique described above may be improved by correcting the extracted LAT values, prior to statistical characteristics calculation, for expected changes in value due to different spatial positions of the electrodes. For example, the wave through the heart can be assumed to travel at a given speed (e.g., 1 m/s). Using the known positions of the electrodes acquiring the signals, theoretical differences in LAT can be applied when calculating the mean.

Figure 4:
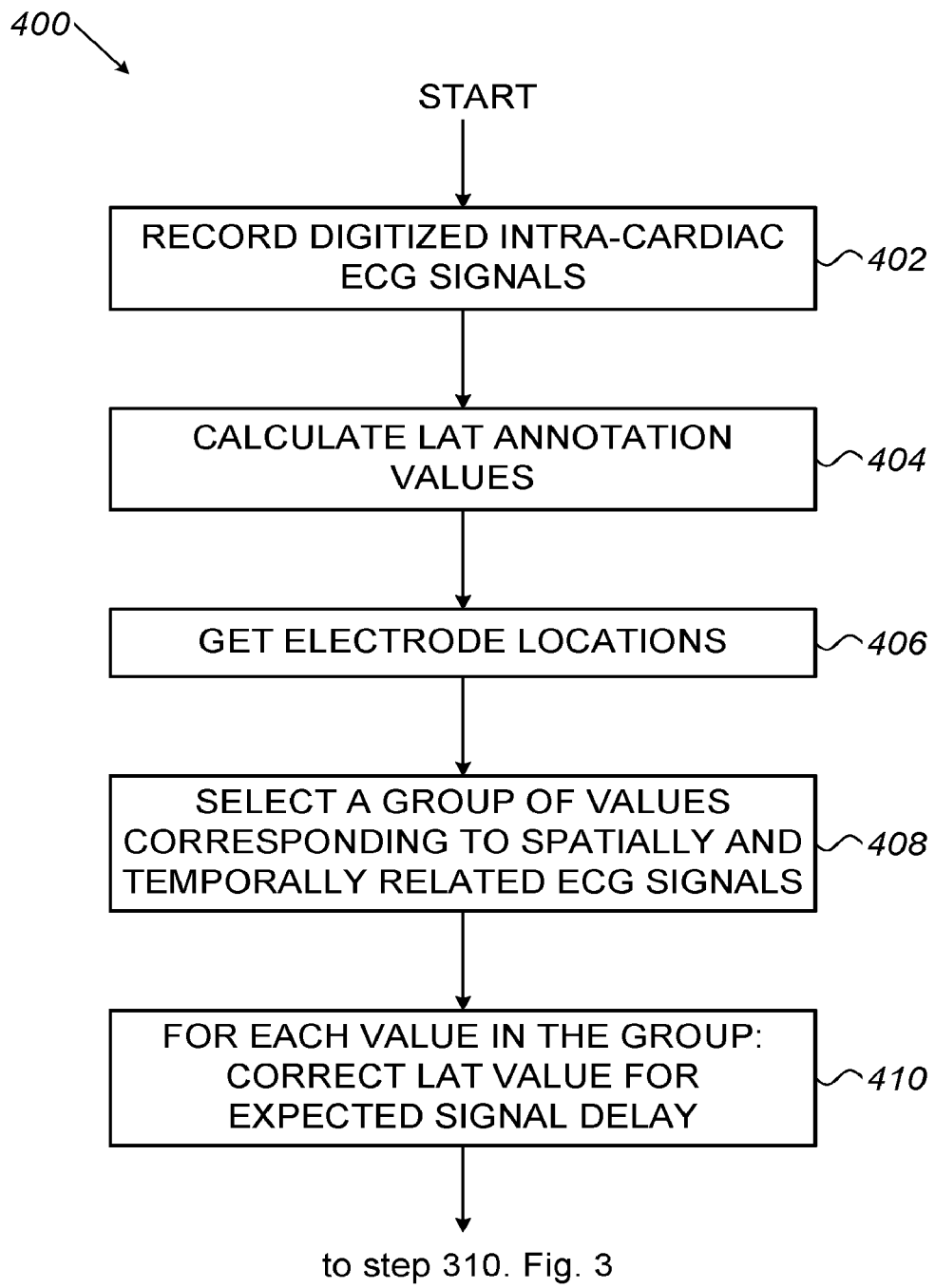
FIG. 4 is a flow chart that schematically illustrates an improved method for enhancing the reliability of annotation values, in accordance with an embodiment of the present invention.

FIG. 4 is a flow chart 400 that schematically illustrates an improved method for enhancing the reliability of annotation values, according to embodiments of the present invention. The flow is executed by processor 34 (FIG. 1). The flow starts at a Recording Signals step 402, followed by a Calculating Annotation Values step 404, a Getting Electrodes Location step 406 and a Selecting Group step 408, which may be identical, respectively, to steps 302, 304, 306 and 308 (FIG. 3).

Next, the processor enters a Correcting LAT Value step 410, wherein, for each LAT value of the group, the processor calculates and applies an estimated correction according to the spatial position of the electrode and the assumed wave travel speed. After step 410, the flow reverts to FIG. 3, at Calculating Mean and SD step 310.

Thus, an estimate of the deviation that is caused by propagation delay can be removed from the group, further enhancing the reliability of the annotation signals.

The example flow chart shown in FIG. 4 is chosen purely for the sake of conceptual clarity. In alternative embodiments, for example, the correction for anticipated signal delay can be integrated in the Calculating Mean and SD step. In other embodiments, the correction is done before the groups are selected (and, thus, groups may comprise a larger number of related LAT values).

Error Propagation and Prevention Thereof

In some embodiments according to the present invention, processor 34 continuously selects groups of related LAT values, responsive to receipt of signals from subsequent heartbeats. In some cases, the processor may select groups of values that correspond to signals that overlap in time. For example, if a first group comprises LAT values extracted from signals that correspond to cardiac cycles n through m and a second group comprises values corresponding to cycles x through y, the groups partially overlap if x>m and y>n.

In the foregoing descriptions, with reference to FIGS. 5A-5C, 6A-6E and 7, we will refer to LAT values that are annotated from different cardiac cycles; each of the LAT values may, in fact, comprise a plurality of spatially related LAT values (including LAT values that have been corrected for signal propagation delay). For simplicity, however, we will show a single LAT value for every cardiac cycle.

FIGS. 5A-5C are timing diagrams that describe events along a horizontal time-axis (not shown). FIG. 5A is a diagram 500 that schematically illustrates the annotation of a series of LAT values in an electro-anatomical system, according to embodiments of the present invention. In the example embodiment illustrated in FIG. 5A, each group comprises ten LAT values, corresponding to ten consecutive cardiac cycles; each pair of consecutive groups share five common LAT values.

For clarity, in the example illustrated in FIG. 5A, the annotated LAT values may be numerically either close to "X" or close to "Y" (will be referred to, for short, as X values and Y values). As would be appreciated, this simplification by no means limits the scope of the present disclosure; embodiments of the present invention may annotate any suitable set of LAT values.

In the example illustrated in FIG. 5A, the first five LAT values are "X", but, when subsequent intra-cardiac signals are received, the majority of the LAT values is "Y", which implies that the initial annotations and the decision taken for the first group were probably erroneous. As will be described below (with reference to FIG. 5B), in some embodiments according to the present invention no corrective action is employed, and the erroneous decision taken for the first group may propagate to further groups. As will be further described (with reference to FIG. 5C), in other embodiments, a corrective action is taken, and error propagation is prevented.

FIG. 5B is a diagram 510 that schematically illustrates statistical characteristics calculation of the LAT values that the processor receives (in FIG. 5A) when no corrective action is taken, according to embodiments of the present invention. Diagram 510 comprises a Group-1 Averaging scheme 512, a Group-2 Averaging Scheme 514 and a Group-3 Averaging Scheme 516 (as will be demonstrated, Group-4 averaging is identical to Group-2 and Group-3 and is not shown).

Group-1 Averaging scheme 512 represents the averaging of the first ten LAT values. There are seven X values and three Y values and, therefore, the mean will be close to X. Hence, the Y values of the last five samples will be omitted from the subsequent group.

Group-2 Averaging scheme 514, representing the averaging of the LAT values 6 through 15, comprises four X values and three Y values (the two original Y values were omitted). The mean will be, again, close to X. Hence, the Y values of the last five samples will be omitted from the subsequent group. As can be seen, the error from the first group has propagated to the second group.

Group-3 Averaging scheme 516, representing the averaging of LAT values 11 through 20, again, comprises four X values and three Y values, as the two original Y values were omitted, and, again, the average is close to X and the Y values will be omitted. Thus, the error from the first group propagates to this group and will continue to further groups. (According to the example illustrated in FIGS. 5A, 5B, propagation will stop only if a larger majority of subsequent LAT values is Y; for example—80%.)

FIG. 5C is a diagram 520 that schematically illustrates avoidance of error propagation by reapplying omitted values, according to embodiments of the present invention. Diagram 520 comprises a Group-1 Averaging scheme 522, a Group-2 Preliminary Averaging scheme 524, a Group-2 Reassessed Averaging scheme 526 and a Group-3 Averaging scheme 528.

Group-1 Averaging scheme 522 represents the averaging of the first ten LAT values, and is identical to Group-1 Averaging Scheme 512 (FIG. 5B). Again, the average is close to X, and the Y values will be omitted from the next group.

Group-2 Preliminary Averaging scheme 524 is identical to Group-2 Averaging Scheme 514 (FIG. 5B), and, again, the average is close to X and the Y values will be omitted from the next group. However, according to the example embodiment illustrated in FIG. 5C, the frequency in which LAT values are omitted is monitored. As there are now six omitted values from the group of ten samples, the processor decides to reapply the omitted values in the statistical-characteristics calculation. The decision to reapply the omitted values (e.g. group 2 in FIG. 5C, designated by reference 524) is the "corrective action" to be undertaken.

Group-2 Recalculated Averaging scheme 526 includes the omitted Y values in the statistical calculation. There will now be six Y values and four X values in Group-2, the average will be close to Y, and the X values will be omitted from the next group. Group-3 Averaging scheme 528 will now comprise two X values and six Y values; the average will be close to Y and the X values omitted. This pattern will continue to Group-4.

Thus, according to the example embodiment illustrated in FIG. 5C, the processor can stop propagation of errors which may occur due to omissions of values by monitoring the frequency in which values are omitted, and take corrective action which may include recalculating the averages without the omitted values, responsive to the frequency in which values are omitted.

Other embodiments according to the present invention may prevent error propagation by reannotating at least some of the LAT values, responsive to the frequency in which values are omitted. This may be effective when the intracardiac signals are ambiguous and may be interpreted in more than one way.

FIGS. 6A-6E are timing diagrams that describe events along a horizontal time-axis not shown.

FIG. 6A is a diagram that schematically illustrates probabilities of LAT values of a series of signals that are acquired by a group of spatially related electrodes in an electroanatomical system, according to embodiments of the present invention. Each rectangle in FIG. 6A represents the probabilities that the LAT value for the corresponding signal is X (upper number) or Y (lower number). The probability of the first five signals to represent X LAT values is 60%, whereas the probability to represent Y values is 40%. Later signals (relating to later cardiac cycles) have, in most cases, higher Y probability than X probability. The signals are divided to partially overlapping groups (1 through 3) with ten samples in each group, and with overlap of five samples between subsequent groups.

FIG. 6B is a diagram that schematically illustrates annotation of LAT values for Group-1 signals, according to an embodiment of the present invention. The processor annotates X values for six of the samples and Y values for four. The average is close to X, and the processor omits the four Y values (three of the omitted signals, designated by doted-line rectangles, overlap with Group-2).

FIG. 6C is a diagram that schematically illustrates annotation of LAT values for Group-2 signals, according to an embodiment of the present invention. From the five signals that are common with Group-1, the processor has omitted the three signals with higher y probability. Four of the remaining seven values are X values and three are Y values. The average, again, is near X, and the processor may omit the Y values from the next group. However, the processor now determines that the number of omitted values is large (e.g., exceeds a preset limit), and tries to reannotate the LAT values, to reduce the number of omitted values.

FIG. 6D is a diagram that schematically illustrates reannotation of the signals of Group-1, according to embodiments of the present invention. The processor now annotates, for the first five samples, the second most probable value (Y,Y,Y,X,Y for the signals 1 through 5, respectively). The LAT values that are now annotated for the first group will comprise three X values and seven Y values, and the average will be close to Y. The seventh and the ninth values, will now be omitted from the next group.

FIG. 6E is a diagram that schematically illustrates reannotation of Group-2 values following Group-1 reannotation, according to an embodiment of the present invention. As the two X values from the five overlapping signals from Group-1 are not omitted, Group-2 comprises six Y values and two X values. The average is now close to Y, and error propagation is prevented.

The error propagation prevention methods described with reference to FIGS. 5A-5C and 6A-6E are example methods that are cited merely for the sake of conceptual clarity. Embodiments according to the present invention may employ alternative methods for the prevention of error propagation. For example, the lengths of the groups and the overlaps may be any suitable number, including group sizes and/or overlaps that vary in time. In some embodiments, the thresholds may be dynamic. In an embodiment, the processor may not annotate a second most probable LAT value if its probability is less than a preset limit, or, alternatively a limit that is a function of the frequency in which LAT values are omitted.

Lastly, in some embodiments, a combination of reinstating the omitted values and reassessing the annotation may be employed.

Figure 7:
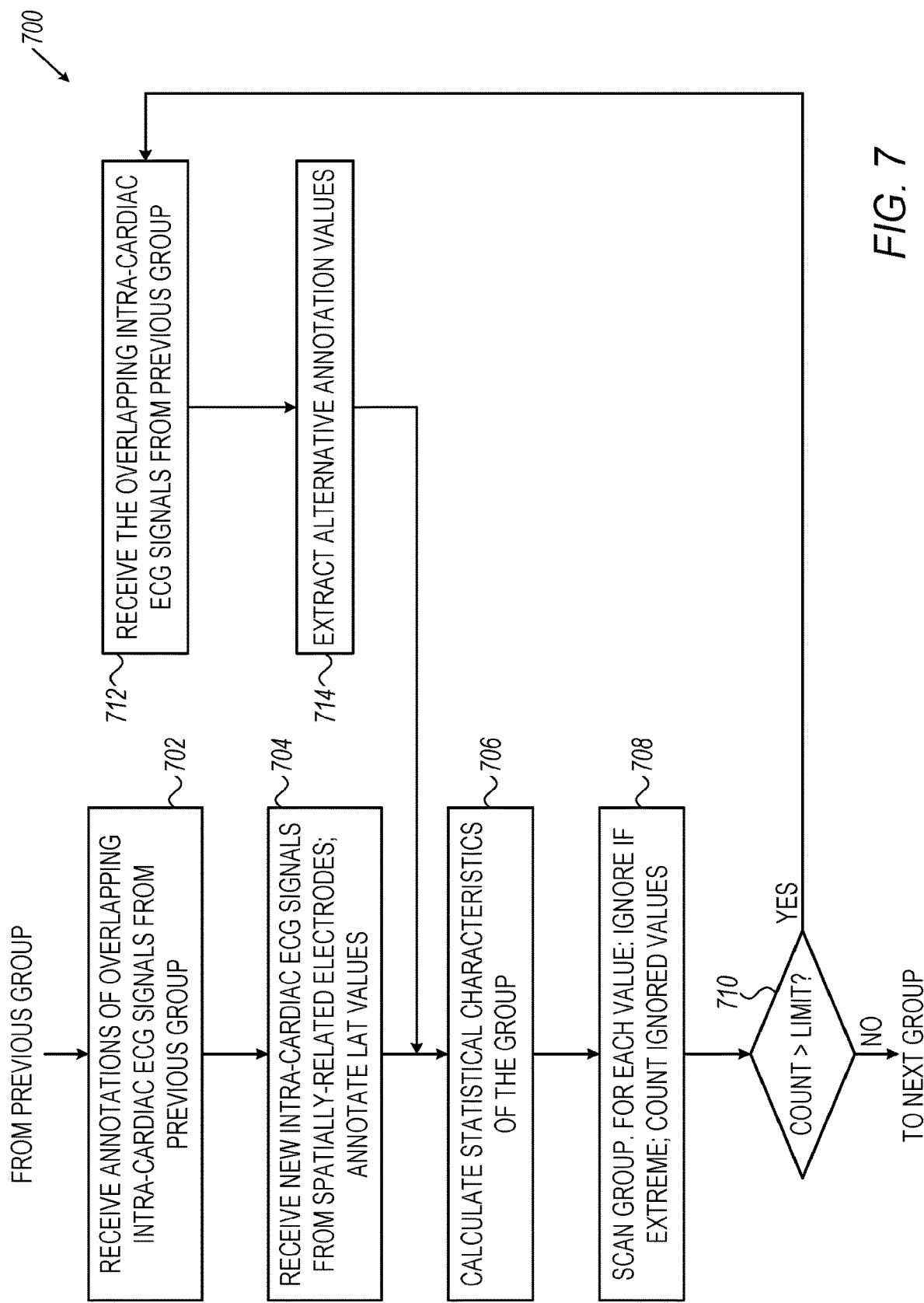
FIG. 7 is a flow chart that schematically illustrates a method for avoidance of error propagation by reannotation, according to embodiments of the present invention.

FIG. 7 is a flow chart 700 that schematically illustrates a method for avoidance of error propagation by reannotation, according to embodiments of the present invention. The flow chart is executed by processor 34 (FIG. 1).

The flow starts at a Receiving Overlapping Annotations step 702, wherein the processor retrieves from memory the annotations of the intra-cardiac ECG signals that are common to the previous group and the current group (as described hereinabove, the processor may omit values which substantially deviate from the mean of the previous group).

Next, at a Receiving New ECG Signals step 704, the processor receives ECG signals pertaining to subsequent cardiac cycles from the electrodes (via acquisition circuitry 36 (FIG. 1)) and annotates the corresponding LAT values. The processor then enters a Calculating Statistics step 706, and calculates statistical characteristics (e.g., mean and standard deviation) of the group of values, which comprises the overlapped values from the previous group and the newly annotated values.

The processor then enters a Scanning Group step 708, wherein the processor compares each of the LAT values of the group to the group-mean (that was calculated in step 706), and omits values which deviate from the mean by more than a preset threshold (or, alternatively, omit values if the standard score is not within preset limits). The processor also counts the number of omitted LAT values.

Next, the processor enters a Comparing Counter step 710, wherein the processor compares the number of omitted values to a preset limit. If the number of omitted values does not exceed the limit, the processor proceeds to the next group (e.g., returns to step 702).

If, in step 710, the number of omitted values has exceeded the preset limit, the processor assumes that an error propagation has occurred, as a result of erroneous annotation of previous LAT values. The processor then enters a Receiving Overlapping Signals step 712 and retrieves the overlapping signals from memory. Next, the processor enters an Extracting Alternative Values step 714, and re-annotates the LAT values from the signals. Since the processor has already annotated the LAT values (in step 704 of the previous group), the processor now looks for an alternative annotation (e.g. the second most probable LAT value of each signal).

After step 714, the processor reenters step 706, and recalculates the statistics with the alternative annotation values. The new values will take effect if the number of omitted values is now smaller than the previous count of step 708.

In summary, according to the example embodiment illustrated in FIG. 7, LAT values of consecutive groups of related intra-cardiac signals are annotated. If an error occurs in a first group, the processor may detect that values in subsequent groups are frequently omitted. The processor then tries an alternative annotation of the signals and selects the LAT values that correspond to the alternative annotation if a fewer number of omitted annotations is achieved.

The example flow chart shown in FIG. 7 is chosen purely for the sake of conceptual clarity. In alternative embodiments, for example, the processor always extracts a first set of most probable annotation values, and a second set of alternative annotation values, and, thus, step 714 is replaced by a Selecting Alternative Values step. In some embodiments, more than two possible LAT values are extracted, and the flow chart is modified accordingly. In an embodiment, step 720, in which the number of omitted values is compared to a threshold, may be replaced by other measures, which compare frequency rather than count. In embodiments, instead of extracting alternative annotations, the processor recalculates the groups statistical characteristics with the omitted values. In yet other embodiments, the processor tries both statistics recalculation and alternative annotation value.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

What is claimed is:

1. A system for optimizing intra-cardiac signals, comprising:
   circuitry configured to receive intra-cardiac signals from one or more electrodes; and
   a processor configured to:
   extract annotation values from the intra-cardiac signals;
   calculate statistical characteristics of the annotation values;
   in response to determining that one or more annotation values are statistically deviant by more than a predefined measure, omit the one or more annotation values;
   assess whether a rate of omission of the one or more annotation values exceeds a predefined threshold; and
   in response to determining that the rate of omission exceeds the predefined threshold, take a corrective action.

2. The system of claim 1, wherein the intra-cardiac signals are received from a medical probe configured to be disposed in a heart of a patient.

3. The system of claim 1 the processor being further configured to determine a mean value of the annotation values, and
   wherein determining that one or more annotation values are statistically deviant includes determining that the one or more annotation values deviate from the mean value by more than a predetermined standard deviation.

4. The system of claim 1, wherein the processor is further configured to group the annotation values into quartiles.

5. The system of claim 4, wherein determining that one or more annotation values are statistically deviant includes determining that the annotation values of one or more intra-cardiac signals are less than a first quartile and greater than a third quartile.

6. The system of claim 5, wherein the first quartile is defined as a value between the smallest annotation value and a median of the annotation values, and
   wherein the third quartile is defined as a value between the largest annotation value and the median of the annotation values.

7. The system of claim 1, wherein the processor is further configured to take the corrective action by re-applying the one or more annotation values omitted from the annotation values and re-determining whether the one or more annotation values are statistically deviant by the predefined measure.

8. The system of claim 1, wherein the processor is further configured to take the corrective action by re-extracting the one or more annotation values from the intra-cardiac signals.

9. The system of claim 1 further comprising a tracking system configured to measure a geometrical location of the one or more electrodes.

10. The system of claim 9, wherein the processor is further configured to:
receive location data from the tracking system, and
calculate deviations of the annotation values over intra-cardiac signals acquired by a selected subset of spatially-related electrodes located no more than a predefined distance from one another in a heart.

11. The system of claim 1, wherein the processor is further configured to average the intra-cardiac signals over multiple temporally-related cardiac cycles that occur within a predefined time duration.

12. The system of claim 1, wherein the processor is further configured to correct one or more of the annotation values in a given intra-cardiac signal, acquired by a given electrode, to compensate for a displacement of the given electrode.

13. The system of claim 1, wherein the annotation values comprise local activation times of the one or more electrodes.

14. The system of claim 1, wherein the processor is further configured to visualize the annotation values by overlaying the annotation values, excluding the one or more annotation values that are statistically deviant, on a model of a heart.

15. The system of claim 1, wherein the one or more annotation values of the intra-cardiac signals are extracted when the intra-cardiac signals are acquired.

16. A method, comprising:
receiving intra-cardiac signals from one or more electrodes;
extracting annotation values from the intra-cardiac signals;
calculating statistical characteristics of the annotation values;
in response to determining that one or more annotation values are statistically deviant by more than a predefined measure, omitting the one or more annotation values;
assessing whether a rate of omission of the one or more annotation values exceeds a predefined threshold; and
in response to determining that the rate of omission exceeds the predefined threshold, taking a corrective action.

17. The method of claim 16 further comprising re-applying the one or more annotation values omitted from the annotation values; and
re-determining whether the one or more annotation values of one or more intra-cardiac signals are statistically deviant by the predefined measure.

18. The method of claim 16 further comprising re-extracting the annotation values from the intra-cardiac signals.

19. The method of claim 16 further comprising measuring a geometrical location of the one or more electrodes.

20. The method of claim 19 further comprising calculating deviations of the annotation values over intra-cardiac signals acquired by a selected subset of spatially-related electrodes located no more than a predefined distance from one another in a heart.

* * * * *